United States Patent
Heismann et al.

(10) Patent No.: US 7,050,533 B2
(45) Date of Patent: May 23, 2006

(54) METHOD AND DEVICE FOR DETERMINING THE TYPE OF FLUID IN A FLUID MASS IN AN OBJECT

(75) Inventors: Bjoern Heismann, Erlangen (DE); Andreas Horst Mahnken, Aachen (DE)

(73) Assignee: Siemens Aktiengesellschaft, Munich (DE)

( * ) Notice: Subject to any disclaimer, the term of this patent is extended or adjusted under 35 U.S.C. 154(b) by 14 days.

(21) Appl. No.: 10/964,916

(22) Filed: Oct. 15, 2004

(65) Prior Publication Data

US 2005/0084063 A1    Apr. 21, 2005

(30) Foreign Application Priority Data

Oct. 15, 2003    (DE) .................. 103 47 971

(51) Int. Cl.
    *G01N 23/87*    (2006.01)

(52) U.S. Cl. .................. 378/53; 378/5; 378/18; 378/57; 378/98.9; 600/407; 600/425

(58) Field of Classification Search .................. 378/53, 378/5, 18, 98.9, 98.11; 600/407, 425
    See application file for complete search history.

(56) References Cited

U.S. PATENT DOCUMENTS

| | | | |
|---|---|---|---|
| 4,029,963 A * | 6/1977 | Alvarez et al. .................. 378/5 |
| 4,247,774 A | 1/1981 | Brooks | |
| 4,540,882 A * | 9/1985 | Vinegar et al. .............. 250/255 |
| 5,164,590 A * | 11/1992 | Coles et al. .................. 250/255 |
| 6,088,423 A * | 7/2000 | Krug et al. .................... 378/57 |
| RE37,899 E * | 11/2002 | Grodzins et al. ............. 378/86 |
| 2004/0218728 A1 * | 11/2004 | Heismann ................... 378/207 |
| 2004/0223585 A1 * | 11/2004 | Heismann et al. ............ 378/54 |

FOREIGN PATENT DOCUMENTS

| | | |
|---|---|---|
| DE | 103 11 628.1 | 3/2003 |
| DE | 101 43 131 A1 | 4/2003 |

* cited by examiner

OTHER PUBLICATIONS

W. Kalender et al., "Materialselektive Bildgebung und Dichtemessung mit der Zwei-Spektren-Methode, 1. Grundlagen und Methodik", Digit. Bilddiagn. 7, 1987, pp. 66-72.

*Primary Examiner*—Allen C. Ho
*Assistant Examiner*—John M. Corbett
(74) *Attorney, Agent, or Firm*—Harness, Dickey and Pierce, PLC

(57) ABSTRACT

A method and a device are proposed for determining the type of fluid in a fluid mass in an object. X-ray attenuation data is supplied from one or a plurality of X-ray recordings of an object area including the fluid mass in the object, which were acquired with at least two different X-ray spectra or detector weightings. The X-ray attenuation data is used to determine values for effective atomic number and density for the fluid mass and average these to obtain a mean value for effective atomic number and density for the fluid mass. Comparison data is also supplied, which indicates fluctuation ranges for combinations of effective atomic number and density for different types of fluid. The mean values for effective atomic number and density of the fluid mass are compared with the comparison data to determine the fluctuation range and thereby the type of fluid, into which the two mean values fall. The method and associated device can be used to determine the type of fluid in a fluid mass in an object in a reliable and unambiguous manner.

14 Claims, 7 Drawing Sheets

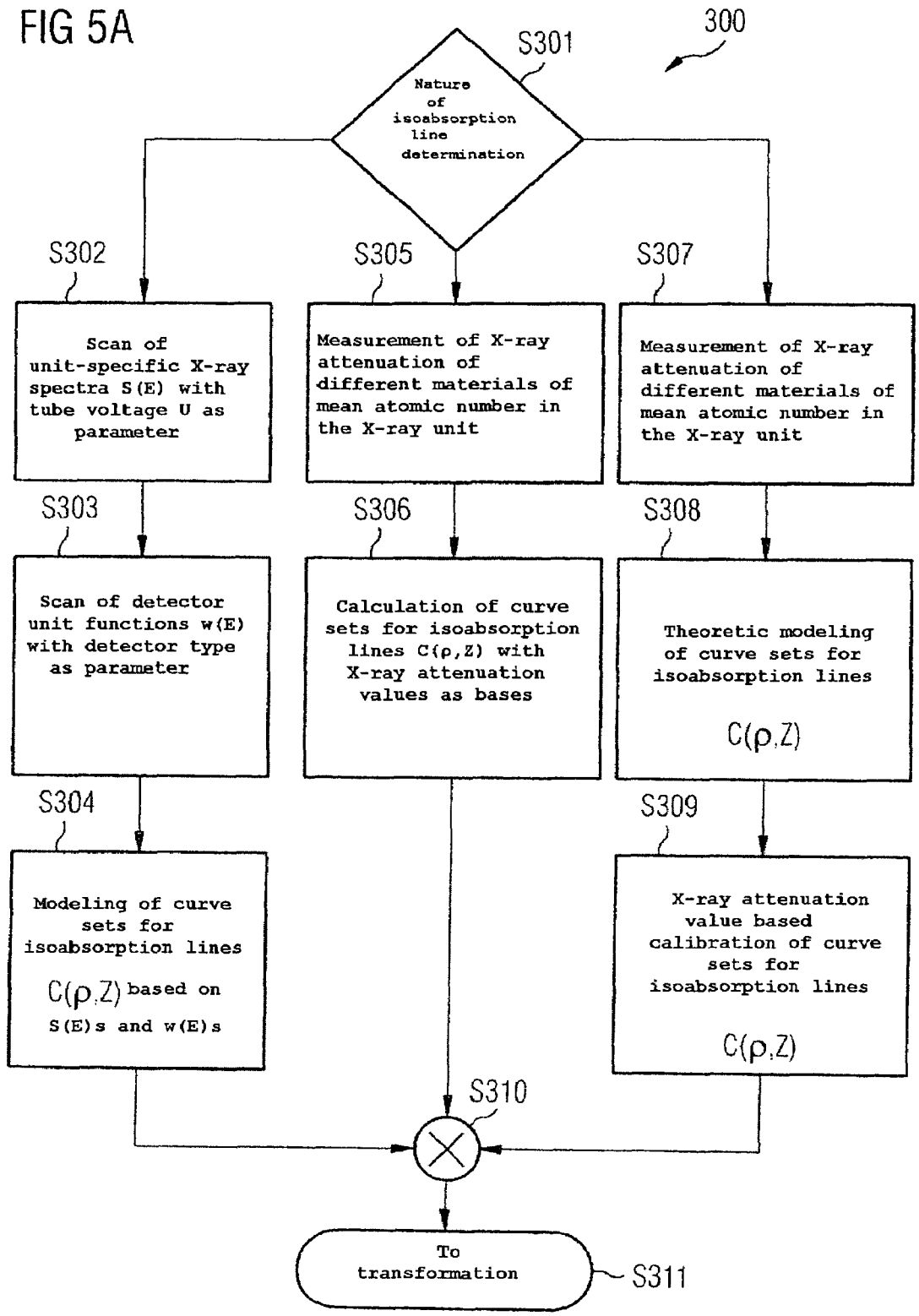

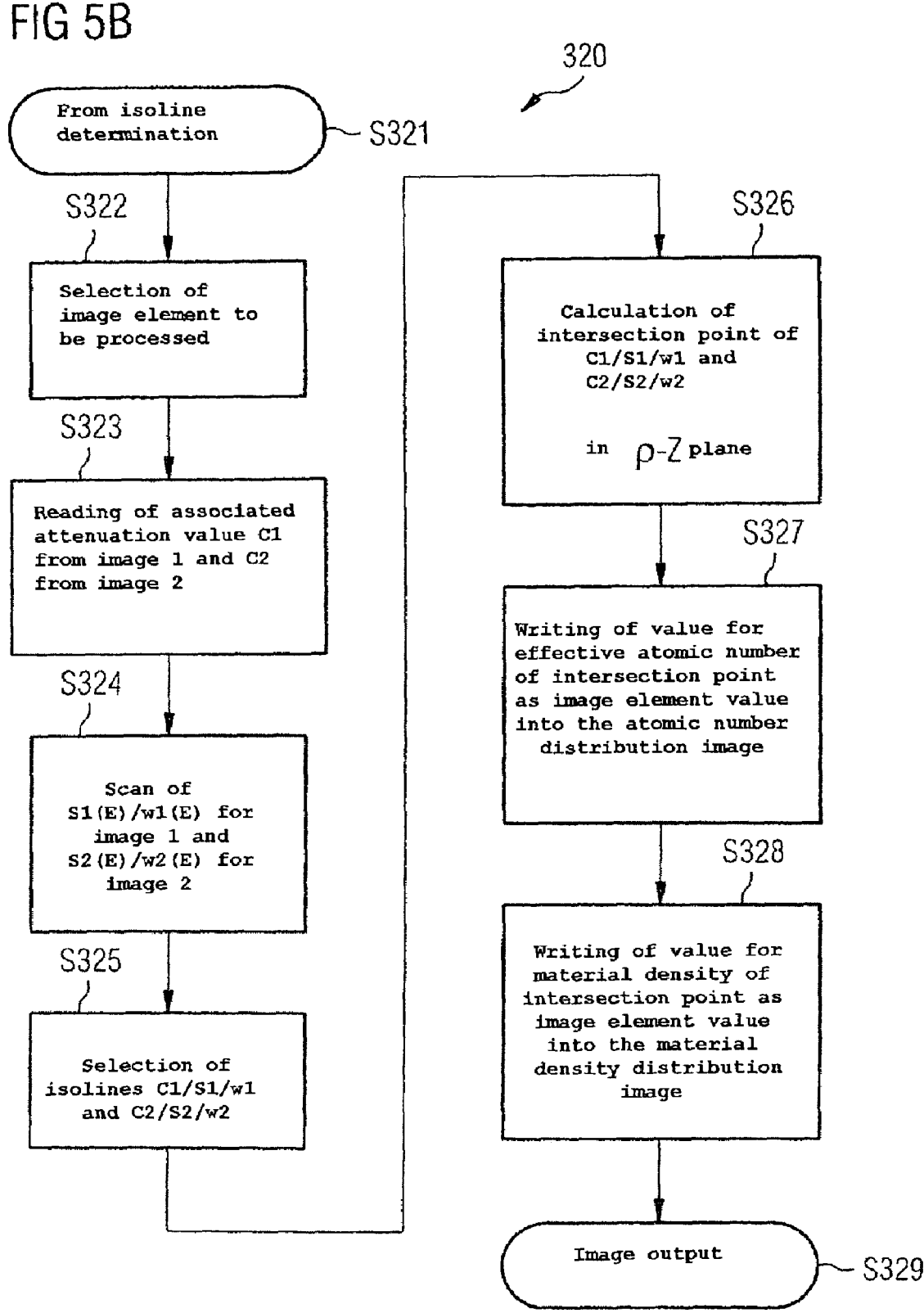

METHOD AND DEVICE FOR DETERMINING THE TYPE OF FLUID IN A FLUID MASS IN AN OBJECT

The present application hereby claims priority under 35 U.S.C. §119 on German patent application number DE 103 47 971.6 filed Oct. 15, 2003, the entire contents of each of which are hereby incorporated herein by reference.

FIELD OF THE INVENTION

The present invention generally relates to a method and a device for determining the type of fluid in a fluid mass in an object by use of X-ray radiation. The method and device are particularly suitable for determining the type of fluid in fluid masses in the bodies of patients.

BACKGROUND OF THE INVENTION

Fluid masses frequently form in the bodies of patients both spontaneously and after major operations. Unambiguous and reliable identification of the type of fluid is important for any necessary treatment of the patient. It is important in particular to differentiate between pus, blood, wound fluid (lymph) and urine. Other possible fluids are for example bile, ascites fluid and exudate in the pleural space. The exact composition of such fluid masses can thereby vary within certain fluctuation ranges.

Generally fluid masses in the body of a patient are identified after a computer tomography (CT) examination in the CT recordings. If the fluid masses are deemed to be critical, an invasive diagnostic procedure, e.g. a puncture or operation is currently required, to differentiate the findings further, in particular to determine the type of fluid.

The result of radiographic methods, e.g. computer tomography, mammography, angiography, X-ray examination techniques or comparable methods is primarily to show the attenuation of an X-ray along its path from the X-ray source to the X-ray detector in a projection image. This attenuation is caused by the material through which the radiation passes along the radiation path, so attenuation can also be understood as the line integral over the attenuation coefficients of all volume elements (voxels) along the radiation path. With tomography methods in particular, e.g. X-ray computer tomography, it is possible to use reconstruction methods to calculate back from the projected attenuation data to the attenuation coefficients $\mu$ of the individual voxels, thereby achieving a considerably more sensitive examination than when simply considering projection images.

A value standardized on the basis of the attenuation coefficient of water, known as the CT number, rather than the attenuation coefficient, is generally used to represent attenuation distribution. This is calculated from an attenuation coefficient $\mu$ currently determined by measurement and the reference attenuation coefficient $\mu_{H2O}$ according to the following equation:

$$C = 1000 \times \frac{\mu - \mu_{H2O}}{\mu_{H2O}} [HU]$$

with the unit Hounsfield [HU] used for the CT number C. For water a value $C_{H2O}=0$ HU results and for air a value $C_L=-1000$ HU. As both representations can be transformed into each other or are equivalent, the generally selected term attenuation value or attenuation value coefficient refers below to both the attenuation coefficient $\mu$ and the CT value.

Although significantly more information is obtained from an image based on the local attenuation coefficient, problems can arise in individual cases when interpreting an image. A locally high attenuation value may for example be due either to materials with a higher atomic number, e.g. calcium in the bones or iodine in a contrast agent or to a high soft-tissue density, as in a lung node. The local attenuation coefficient $\mu$ at location $\vec{r}$ is a function of the X-ray energy E radiated into the respective tissue or material and the local tissue or material density $\rho$ according to the following equation:

$$\mu = \mu(E, \vec{r}) = (\mu/\rho)(E,Z) \times \rho(\vec{r})$$

with the energy-dependent and material-dependent mass attenuation coefficient $(\mu/\rho)(E,Z)$ and the (effective) atomic number Z.

The energy-dependent X-ray absorption of a material, which is determined by its effective atomic number Z, therefore masks the X-ray absorption influenced by the material density $\rho$. Materials or tissue with different chemical and physical compositions, in particular also fluid masses, can therefore have identical attenuation values in the X-ray image. Conversely conclusions cannot be drawn about the material composition of an object under examination from the attenuation value of an X-ray recording.

In the context of this description, unless otherwise specified, the term atomic number is not used in the strict element-related sense but instead refers to the effective atomic number of a tissue or material, calculated from the chemical atomic numbers and atomic weights of the elements involved in the structure of the tissue or material.

It is known from U.S. Pat. No. 4,247,774 in conjunction with computer tomography methods that different X-ray spectra or X-ray quantum energies can be used to generate an image. Such methods are generally referred to as dual spectrum CT. They use the fact that the attenuation coefficient $\mu$ is a function of energy based on the atomic number, i.e. they are based on the effect caused by the fact that materials and tissue with higher atomic numbers absorb lower-energy X-ray radiation to a significantly greater degree than materials or tissue with a lower atomic number. With higher-energy X-ray radiation however the attenuation values correspond and are primarily a function of material density. With dual spectrum CT the differences are calculated for example in the images recorded at different X-ray tube voltages.

Even more specific information is obtained, if the so-called basic material analysis method is used with X-ray recordings, as described by W. Kalender et al. in "Materialselektive Bildgebung und Dichtemessung mit der Zwei-Spektren-Methode, I. Grundlagen und Methodik" (Material-selective imaging and density measurement using the dual spectrum method, I. Basic principles and methods), Digit. Bilddiagn. 7, 1987, 66–77, Georg Thieme Verlag. With this method the X-ray attenuation values of an object under examination are measured with lower and higher energy X-rays and the resulting values are compared with the corresponding reference values for two basic materials, e.g. calcium for bone material and water for soft tissue. It is assumed that every measurement value can be shown as a linear superposition of the measurement values for the two basic materials. Thus the proportion of bone and proportion of soft tissue can be calculated from the comparison with the basic material values for every element in the image of the object under examination, so that transformation of the original recordings into representations of the two basic materials results. Basic material analysis and the dual spectrum method are therefore suitable for separating or differentiating predefined anatomical structures or types of material in human and animal tissue with significantly different atomic numbers.

A method is also known from German patent application DE 101 43 131 A1, the sensitivity and significance of which exceed those of basic material analysis and allow for example extremely informative functional CT imaging. With this method the spatial distribution of the density $\rho$ (r) and the effective atomic number Z (r) are calculated by evaluating the spectrally influenced measurement data of an X-ray unit. A combined evaluation of the distribution of density and the effective atomic number allows body components such as iodine etc. to be determined quantitatively and for example calcification to be segmented out based on the atomic number. However the hitherto known methods do not allow reliable determination of the type of fluid in fluid masses in the body of the object under examination.

SUMMARY OF THE INVENTION

An object of an embodiment of the present invention is to specify a method and a device for determining the type of fluid in a fluid mass in an object, which can be used to identify the type of fluid in an unambiguous and reliable manner.

With the present method of an embodiment for determining the type of fluid in a fluid mass in an object, in particular in an area of the body of a patient, X-ray attenuation data is supplied from one or a plurality of X-ray recordings of an area of the object including the fluid mass in the object, acquired with at least two different X-ray spectra or spectral detector weightings. Values for effective atomic number and density are determined for the fluid mass from the X-ray attenuation data and averaged to obtain a mean value for the effective atomic number and density of the fluid mass. Comparison data is also supplied, indicating the fluctuations ranges for combinations of effective atomic number and density for different types of fluid. The mean values for effective atomic number and density of the fluid mass are compared with the comparison data to determine the fluctuation range, into which the two mean values fall. Finally from this comparison the fluid type of the comparison data is defined as the fluid type of the fluid mass, which is assigned to the fluctuation range determined in the comparison data.

The associated device for determining the type of fluid of a fluid mass in an object includes at least an X-ray source for emitting X-ray radiation and a plurality of X-ray detectors facing the X-ray source to acquire X-ray attenuation data for an object arranged between the X-ray source and the X-ray detectors and an evaluation unit for converting electrical signals from the X-ray detectors to X-ray attenuation data. The device is characterized in that the evaluation unit includes a module for fluid determination, which uses X-ray attenuation data from one or a plurality of X-ray recordings of an object area including the fluid mass in the object, acquired using at least two different X-ray spectra or detector weightings, to determine values for the effective atomic number and density for the fluid mass and averages these to obtain a mean value for the effective atomic number and a mean value for the density of the fluid mass and compares the mean values with comparison data in a storage unit, which indicates the fluctuation ranges for combinations of effective atomic number and density for different types of fluid, to determine the fluctuation range into which the two mean values fall. The evaluation unit module is also configured such that it outputs to the operator a reference to the fluid type, which is assigned to the fluctuation range defined automatically by comparison.

The term X-ray spectrum used in the present description has a broader meaning than just the spectral distribution of X-ray radiation emitted from the X-ray source of the device. Different spectral parts of the radiation can also be converted with differing degrees of efficiency on the part of the X-ray detector and can thereby be weighted differently. The resulting effective spectral distribution is also referred to in the present patent application as the X-ray spectrum.

With the proposed method of an embodiment of the present application, the types of fluid in the respective fluid masses can be unambiguously identified from the X-ray attenuation data from one or a plurality of X-ray recordings of the object area of interest, preferably using the technique of determining the spatial distribution of density and the effective atomic number known from DE 101 43 131 A1 (the entire contents of which are hereby incorporated herein by reference), from at least two X-ray recordings with different X-ray spectra. Comparison data is used for this, which only has to be determined once on the basis of corresponding preliminary measurements.

For these preliminary measurements a sufficiently large number of specimens of a specific body fluid, preferably 6 or more specimens, are measured using the different X-ray spectra also used for the subsequent recordings and the values for density and atomic number for these specimens are determined from the X-ray attenuation data obtained using the above-mentioned technique. The preliminary measurements are carried out with different body fluids occurring typically as fluid masses in the body of a patient.

Due to the fluctuating composition of such body fluids these preliminary measurements are used to obtain different combinations of density and effective atomic number. Fluctuation ranges for these combinations of effective atomic number and density are then determined for the respective fluid type, within which the measured values for the associated fluid type lie. The fluctuation ranges and assigned fluid types obtained from these preliminary measurements are supplied as comparison data with the present method of an embodiment and with the associated device.

To implement the method of an embodiment, the X-ray attenuation data is also supplied from one or a plurality of X-ray recordings of an object area including the fluid mass in the object, which were acquired using the at least two different X-ray spectra. Naturally the recording of said X-ray images can also be a component of the present method of an embodiment. In the present patent application X-ray attenuation data refers to the attenuation values obtained from the recordings, i.e. either the attenuation coefficients $\mu$ directly or the CT number C that is a linear function of these. This X-ray attenuation data in each instance indicates the spatial distribution of the attenuation values, from which a spatial distribution of effective atomic numbers and a spatial distribution of density can be obtained by evaluation. Details of the associated technique can be obtained from DE 101 43 131 A1, the entire content of which is specifically incorporated by reference in the present patent application.

With the present method of an embodiment, at least the values for effective atomic number and density for the area of the fluid mass in the X-ray attenuation data are preferably determined using the technique and averaged using the data. In this way, a mean value is obtained for the effective atomic value and a mean value for the density of the fluid mass. Depending on the type of X-ray recordings taken, e.g. X-ray CT recordings or simple X-ray fluoroscopy, this averaging operation includes either a three-dimensional or two-dimensional data field. Comparing the effective atomic number thus averaged and the averaged fluid mass density with the comparison data allows the defined area in the comparison data, into which these mean values fall, and therefore the type of fluid in the fluid mass, to be determined unambiguously.

The present method of an embodiment can thereby be implemented both in-vivo and in-vitro. It is of course also possible to determine fluid masses in non-human or animal bodies using the method and the device.

The two attenuation value distributions represented by the X-ray attenuation data do not necessarily have to be recorded consecutively as two recordings with different X-ray voltages. As each X-ray tube emits a spectrum of a certain width, with an appropriate spectrally selective configuration of the associated receiver unit, it is possible to record the two attenuation value distributions largely or completely simultaneously. For this purpose for example filters that can be inserted into the radiation path and/or two separate X-ray detector arrays can be used. The receiver unit can also be equipped with a quantum-energy-selective X-ray detector array to implement the method.

The density values and effective atomic numbers of the fluid masses are determined from the X-ray attenuation data, preferably using the technique of the aforementioned DE 101 43 131 A1. Here a first functional dependency of a first attenuation value of the first attenuation value distribution, i.e. the X-ray attenuation data recorded with the first X-ray spectrum, on density and atomic number is determined and at least a second functional dependency of a second attenuation value of the second attenuation value distribution assigned to the first attenuation value, i.e. the X-ray attenuation data recorded with the second X-ray spectrum, on density and atomic number is determined. A comparison of the first functional dependency and the second functional dependency and where necessary further functional dependencies is used to determine the spatial atomic number distribution and the spatial density distribution at least in the area of the fluid mass. Determination of the functional dependency of the attenuation values on density and atomic number is preferably determined here for at least one X-ray spectrum using reference measurements taken on a calibration specimen or in the form of a simulation based on a physical model.

In another embodiment, the attenuation value distributions are converted to a density distribution and an atomic number distribution for each of the assigned attenuation values of the first attenuation distribution and the further attenuation distributions based on the determination of a value pair for density and atomic number such that the value pair satisfies the previously determined functional dependencies of X-ray absorption on density and atomic number for the first X-ray spectrum and at least one further X-ray spectrum. In this way, density and atomic number for an image element can simply be calculated as the intersection of the functional dependencies of the attenuation values assigned respectively to each other for the recorded distributions of the attenuation values.

The first X-ray spectrum advantageously has a quantum energy, which compared with the quantum energy of the second X-ray spectrum favors X-ray absorption due to the photoelectric effect, so that high resolution is achieved in the determination of atomic numbers.

In another embodiment, in order to change an X-ray spectrum to record the object, at least one operating parameter of the X-ray tube is changed, whereby the X-ray source in a first operating state emits a first X-ray spectrum and in a second operating state emits a different second spectrum, thereby allowing a fast change between two X-ray spectra.

Also in order to change an X-ray spectrum to record the object, the detector characteristics can be changed, whereby the X-ray detector converts spectral subareas of the X-ray radiation received from the X-ray source to mutually independent electrical signals, thereby allowing simultaneous recording of attenuation value distributions with different X-ray spectra.

BRIEF DESCRIPTION OF THE DRAWINGS

Further advantages, features and characteristics of the present invention are now explained in more detail on the basis of illustrative exemplary embodiments and with reference to the attached drawings, which are given by way of illustration only and thus are not limitative of the present invention, and wherein:

FIG. 5a shows an exemplary function diagram of a calculation method for determining isoabsorption lines as part of the method according to FIG. 3;

FIG. 5b shows an exemplary flow diagram of the transformation of the X-ray attenuation data into values for material density and atomic number as part of the method according to FIG. 3;

DETAILED DESCRIPTION OF THE EXEMPLARY EMBODIMENTS

Figure 1:
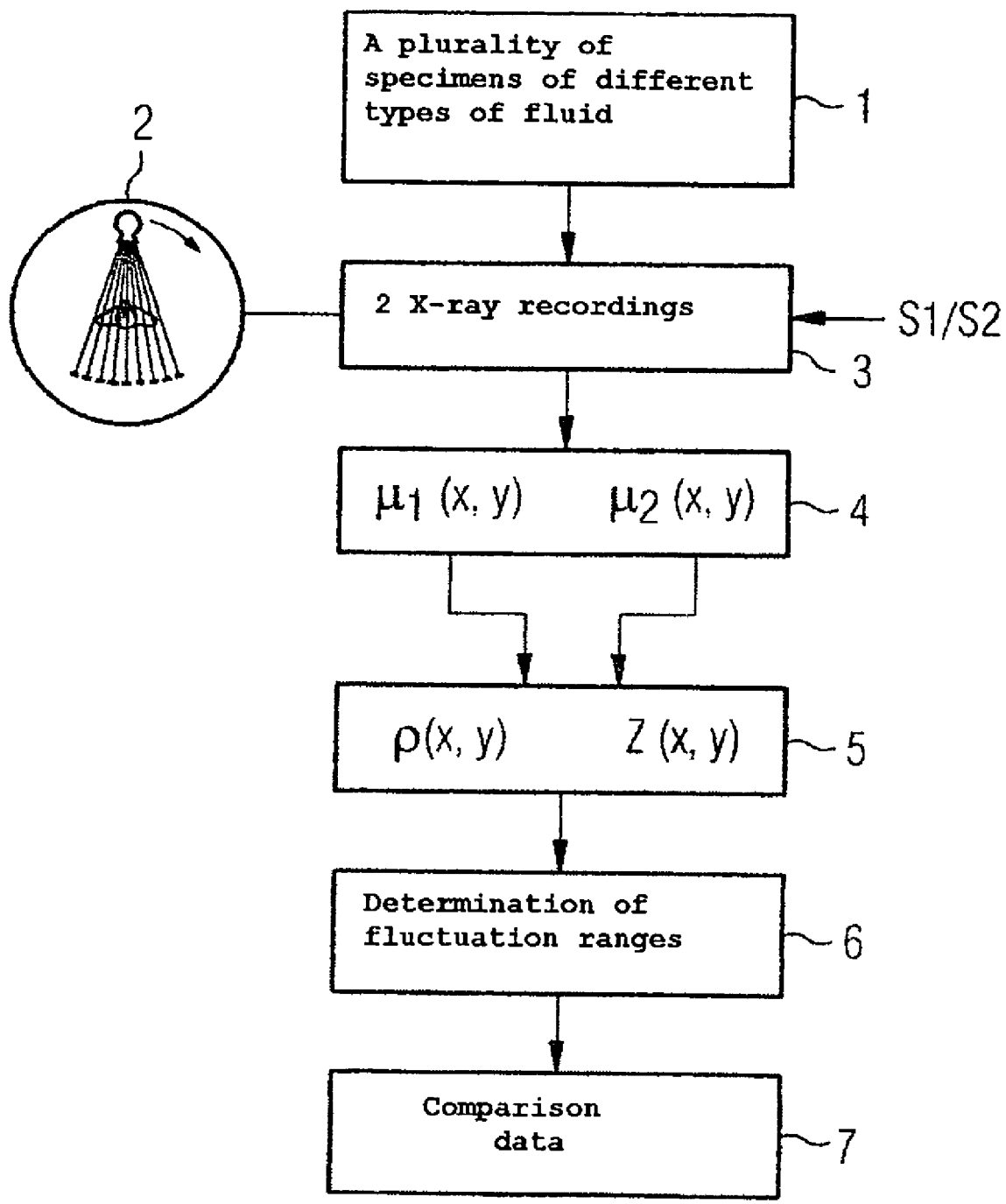
FIG. 1 shows a flow diagram for generating the comparison data for an embodiment of the present method.

FIG. 1 shows an exemplary embodiment for the generation of comparison data, as deployed with the present method, and the associated device. In a first step 1 specimens of different fluid types are supplied, as occur as fluid masses in the body of a patient. Examples of such fluid types are water, blood, blood with coagulants (citrate/EDTA), pus, pus containing a high proportion of blood, drainage fluid from an intestinal procedure, urine, bile or wound fluid. A sufficient number of specimens (>5) are provided for each of these types of fluid.

In the next step 3 these specimens are examined in an X-ray computer tomograph 2 (only shown in outline), whereby X-ray recordings are taken respectively using a first X-ray spectrum S1 and—simultaneously or consecutively—using a second X-ray spectrum S2. Using image reconstruction (third step 4) based on the raw data thus obtained, an attenuation value distribution is generated for each of the X-ray spectra S1, S2, e.g. as distribution $\mu_1(x, y)$ and $\mu_2(x,$ y) of the attenuation coefficient μ within a transverse layer image with coordinates x and y. In a fourth step 5 the distributions $\mu_1$ (x, y) and $\mu_2$ (x, y) of the attenuation coefficient are transformed using a computer into an atomic number distribution Z (x, y) and a density distribution ρ(x, y). This is carried out for all the specimens provided.

Due to fluctuations in the composition of the plurality of specimens of a fluid type, different density and atomic number values are obtained for the respective fluid type in this way. In step 6 a fluctuation range is established for each of these fluid types based on the density and atomic number data obtained, within which range the different combinations of density and atomic number for the respective fluid type lie. The fluctuation ranges thus established are then supplied as comparison data (step 7), in particular stored in a storage unit. The comparison data hereby contains the established fluctuation ranges and the respectively assigned fluid type.

Figure 2:
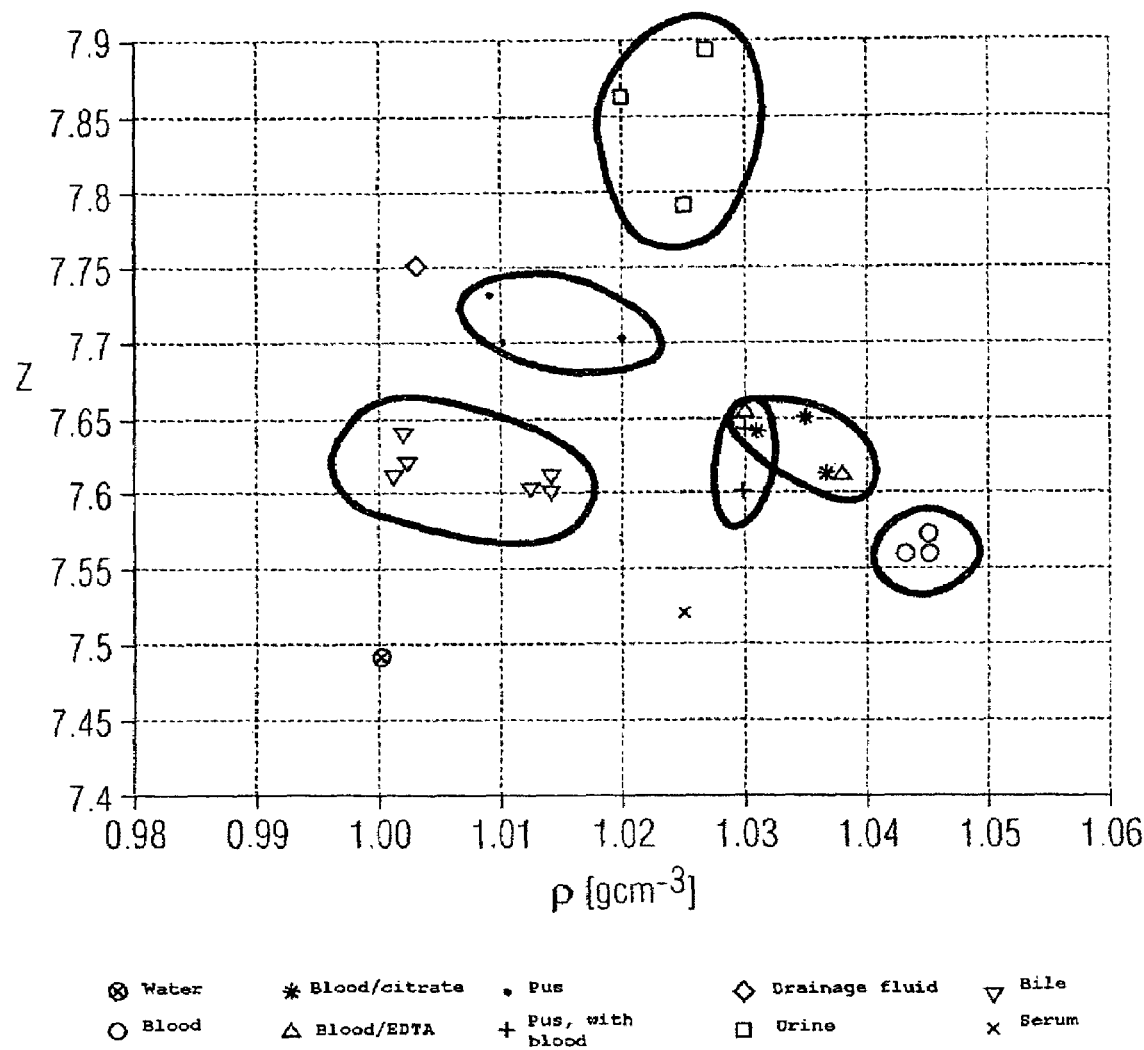
FIG. 2 shows an example of the definition of different fluctuation ranges for the combination of density and effective atomic number for different types of fluid with reference to a Z-$\rho$ diagram.

FIG. 2 shows an example 1 of the combinations of density and atomic value obtained in this manner for different fluid types and the established fluctuation ranges based on these with reference to a Z-ρ diagram. The Figure hereby shows that to some degree fluctuating distribution of the atomic numbers and density values for water, blood, blood with citrate, blood with EDTA, pus, pus containing blood, drainage fluid, urine, bile and serum. Clustering is carried out on the basis of this data, i.e. fluctuation ranges are established, in which the respective density and atomic number values for the associated fluid lie or fluctuate. The established ranges are shown in FIG. 2 with the respective lines. The measurement accuracy relating to ρ and Z is adequate with these in-vitro values to be able to carry out clustering and thereby to differentiate the fluids in question.

The comparison data for implementing an embodiment of the present method only has to be supplied once. The correspondingly stored comparison data can then be used for a plurality of examinations.

Figure 3:
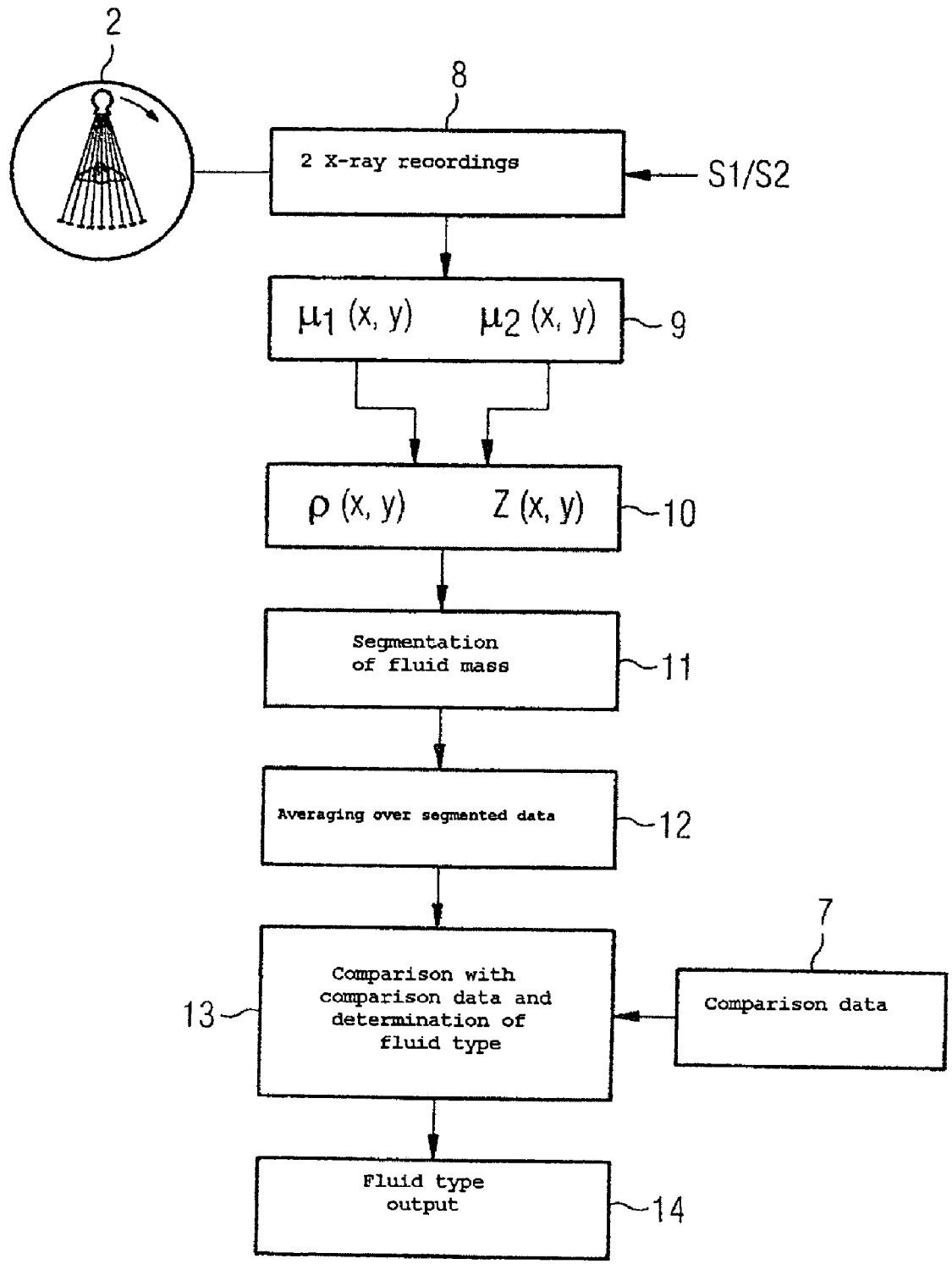
FIG. 3 shows a flow diagram of the present method according to an exemplary embodiment.

FIG. 3 shows a schematic illustration of a flow diagram according to an exemplary embodiment of the present method. The patient is examined here in the X-ray computer tomograph 2 (only shown in outline here too) in step 8, whereby here too, as already described in relation to FIG. 1, X-ray recordings are taken with the two different X-ray spectra S1 and S2. These two X-ray spectra must be identical to the X-ray spectra with which the comparison data was recorded. The X-ray computer tomograph 2 must therefore be operated with identical operating parameters.

Here too image reconstruction (second step 9) based on the raw data obtained is used to generate an attenuation value distribution $\mu_1$ (x, y) and $\mu_2$ (x, y) of the attenuation coefficient μ for each of the X-ray spectra S1 and S2 within a transverse layer image with the coordinates x and y. The patient's X-ray recordings can of course thereby cover both a larger area, within which the fluid mass lies, and an object area encompassing the fluid mass more closely.

In step 10 a computer is used again to transform the distributions $\mu_1$ (x, y) and $\mu_2$ (x, y) of the attenuation coefficient into an atomic number distribution Z (x, y) and a density distribution ρ (x, y). In step 11 the two dimensional area in the present example, which corresponds to the fluid mass or identifies the associated two-dimensional data field is segmented into density and atomic number data. This can for example be achieved using a graphic representation of the data, in which the corresponding area is marked by a user. It is also possible to segment based on predefined density and atomic number values and this is carried out automatically with computer assistance when the values have been input. In the case of a three-dimensional data field the 3D volume corresponding to the fluid mass or the associated density and atomic number data is segmented correspondingly.

In step 12 mean values are calculated for the density values and atomic number values in the thus segmented or defined volume or the corresponding area. This gives a mean density and a mean atomic number for the fluid mass.

This mean density and mean atomic number are compared in step 13 with the comparison data supplied by step 7. During the course of this comparison it is ascertained in which of the fluctuation ranges established in the comparison data the combination of mean atomic number and mean density falls, thus obtaining the associated fluid type (step 14). With the associated exemplary device according to FIG. 7 the fluid type thus determined is output on a monitor.

Naturally the present method can not only be implemented with X-ray computer tomographs but also with other X-ray equipment, e.g. C-arm units or simple X-ray fluoroscopy devices with digital image processing.

Figure 4:
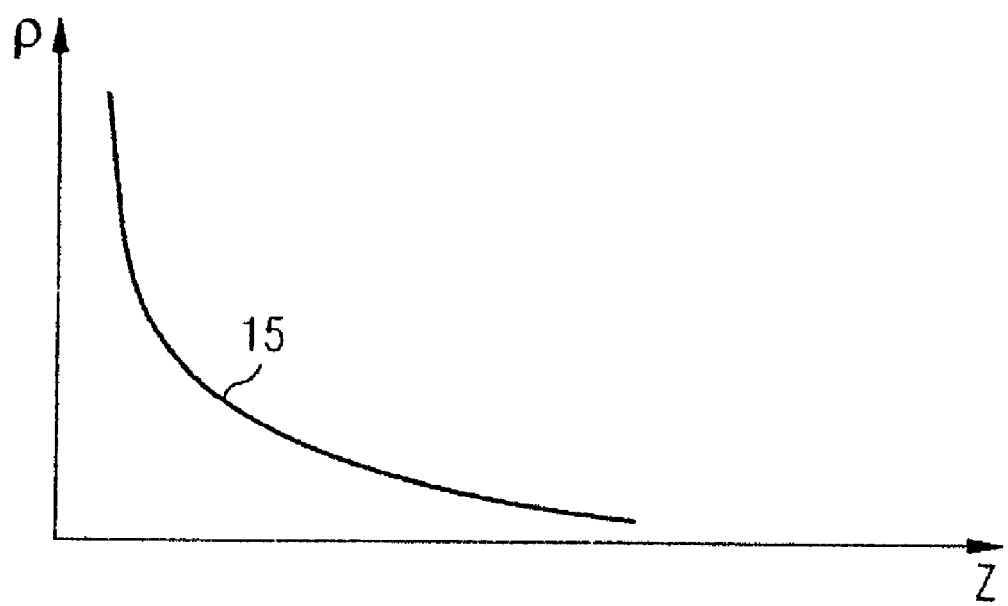
FIG. 4 shows the occurrence of identical attenuation value in materials of different composition with reference to an isoabsorption line.

The computer-assisted transformation of the attenuation value distributions into an atomic number distribution and a density distribution according to steps 5 and 10 in FIGS. 1 and 3 can for example be carried out with the method from DE 101 43 131 A1, to which specific reference is made. This technique is explained again in more detail with reference to the following FIGS. 4 to 6. The isoabsorption line 15 in FIG. 4 connects all the value pairs (ρ, Z) with an identical attenuation value μ or C with a defined X-ray spectrum. This identical attenuation value for different materials is due to the fact that attenuation mechanisms act in different ways due to the material itself, the material density and the energy of the X-ray radiation. This results in the different combinations of density and atomic number shown in FIG. 4, each of which produces the same attenuation value during an X-ray recording.

The effective atomic number Z of a specific type of tissue or a specific material referred to in the context of this description for simplicity as the atomic number is calculated from the atomic numbers $Z_i$ of the elements involved in the structure, their atomic weights $A_i$ and their local material-equivalent densities ρi for example as follows:

$$Z = \left\{ \frac{\sum_i \frac{\rho i}{Ai} \rho i Z_i^4}{\sum_i \frac{\rho i}{Ai} \rho i} \right\}^{\frac{1}{3}}$$

Calculation of the atomic number and density distributions in an object area requires at least two X-ray recordings of the area taken with identical recording geometry but different energy values for the X-ray radiation used. The use of more than two X-ray recordings recorded with different X-ray energy values can improve the Z and ρ resolution but it also increases the radiation load. This is therefore not always an option when examining a patient.

The starting point for converting image data based on attenuation values to distribution images for atomic numbers and material or tissue density is knowledge of the isoabsorption lines for every X-ray spectrum of an X-ray unit. As mentioned above, X-ray spectrum here does not refer to the narrow concept of the spectral distribution of X-ray radiation emitted by the radiation source of the unit but a broader concept, which takes into account the different weightings of the different spectral ranges of the emission spectrum of the X-ray tube on the part of the X-ray detectors. A measured attenuation value therefore results from the direct attenuation of the radiation spectrum emitted by the X-ray tube and the spectral efficiency of the X-ray detectors used. Both values are unit-specific variables and must therefore be determined either directly or indirectly using the attenuavalues of calibration specimens. These are the basis for calculating the isoabsorption lines.

FIG. 5a outlines three methods 300 for modeling or calculating a set of isoabsorption lines. These are theoretical modeling, experimental determination and theoretical modeling with curve calibration using experimentally determined parameters.

In principle as many isoabsorption lines should be determined as attenuation values are required to cover the span of X-ray attenuation values in the X-ray recordings. It is not necessary to calculate an isoabsorption line for every theoretically occurring attenuation value; isoabsorption lines not worked out can be provided if necessary by interpolation or other appropriate averaging methods.

The basic steps of theoretical modeling are shown in the left branch of the flow diagram in FIG. 5a. In step S302 the data for the X-ray emission spectra S(E) specific to a unit are first read in with the available tube voltages as a parameter. The spectral distributions of the X-ray radiation can be measured beforehand for this purpose by way of experiment for each individual X-ray unit or characteristic data is used for a specific type of X-ray source. The detector unit function w(E) is determined in step S303. For this purpose too precise measurement of the detector arrangement can be undertaken beforehand or data characterizing the type of detector e.g. its spectral technical specification can be used. The isoabsorption lines are calculated in the form of curve sets $C_i$ ($\rho$, Z) and $\mu_i$ ($\rho$, Z) based on a physical model in step S304, which simulates the X-ray attenuations $C_i$ and $\mu_i$ for materials with different atomic numbers and with different material densities for every relevant combination of S(E) and w(E).

As an alternative to the theoretical modeling in steps S302 to S304 the curve sets of the isoabsorption lines can also be determined by experiment. For this the X-ray attenuation values of calibration materials of different density and with a mean atomic number are measured in the X-ray unit with different relevant combinations of S(E) and w(E) in step S305. The measured values form the bases for subsequent calculation of the curve sets for isoabsorption lines $C_i$ and $\mu_i$ in step S306.

In a further alternative, the curve sets $C_i$ and $\mu_i$ modeled on a theoretical basis are calibrated using X-ray attenuation values determined by experiment. In step S307 the attenuation values required to calibrate the theoretical curve sets are measured as described above for step S305 using appropriate calibration materials or phantoms in the X-ray unit. In contrast to the purely theoretical modeling in steps S302 to S304 with this method a precise knowledge of the X-ray emission spectra S(E) and w(E) is not required but parameters are required for the theoretical modeling of the curve sets for isoabsorption lines $C_i$ and $\mu_i$ in step S308. Calibration of the curves in step S309 using the calibration values determined by experiment in step S307 then defines values for these parameters, which are specific to the X-ray emission spectra and detector unit functions of the X-ray unit.

Determination of the isoabsorption lines for the necessary X-ray attenuation values and combinations of S(E) and w(E) creates the preconditions for the transformation of image data, which represents the attenuation values of the X-ray radiation as it passes through tissue, into image data, which represents the distribution of the atomic number or material density in corresponding tissue.

Depending on the task to be carried out, the three methods for determining isoabsorption lines can also be used in combination. For example values, which can only be determined imprecisely or with a great deal of time and effort or cannot be determined at all by experiment, can be supplemented or made more precise by theoretical modeling. Data obtained using different methods is then merged into a standard data record in step S310 and is supplied for image transformation purposes in step S311.

FIG. 5b shows an appropriate transformation method 320 for the inventive method. It is based on the curve sets for isoabsorption lines determined according to the method 300 described above and supplied as a data record in step S321.

Transformation is effected by image element. A transformation of an X-ray attenuation value distribution based on two X-ray images recorded with different X-ray energy spectra but identical recording geometries is used as a basis below. This is the minimum condition for carrying out such a transformation. However more than two X-ray recordings can also be used with more than two different energy distributions of the X-ray radiation.

The image element to be transformed is selected in step S322 and in the next step S323 the attenuation values $C_1$ and $\mu_1$ for this image element are read from the first X-ray image and $C_2$ and $\mu_2$ from the second X-ray image. In the next step S324 the X-ray radiation spectrum $S_1$ (E) used for the first X-ray recording and the detector unit functions $w_1$ (E) and the corresponding values $S_2$ (E) and $w_2$ (E) for the second X-ray image are scanned. These values form the parameters for subsequent selection of the isoabsorption lines to be assigned to the respective attenuation values. The spectral distributions $S_i$ (E) and $w_i$ (E) can also be determined indirectly here, e.g. by scanning the X-ray voltages $U_1$ and $U_2$ used or the operating parameters of the X-ray detectors.

Figure 6:
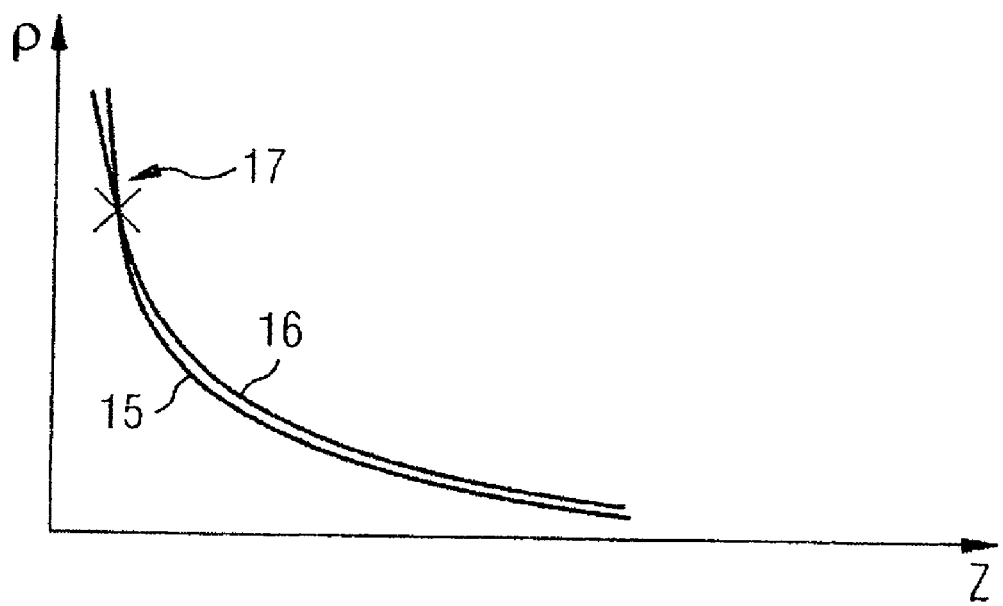
FIG. 6 shows two isoabsorption lines of a material with two different X-ray spectra.

In step S325 the data record of isoabsorption lines supplied in step S321 is used to select a first curve, which satisfies the conditions $C_1$ and $\mu_1$ with the parameters $S_1$ (E) and $w_1$ (E), and a second curve, which satisfies the conditions $C_2$ and $\mu_2$ with the parameters $S_2$ (E) and $w_2$ (E) . An example of a first isoabsorption line 15 obtained in this way and a second 16 isoabsorption line is shown in FIG. 6.

The point of intersection 17 is calculated as the intersection of the two curves 15 and 16 in step S326. The curve intersection 17 can be determined for example by a local linear transformation or by iterative determination of the point of intersection. As the two curves 15 and 16 represent two different attenuation values for the same image element and therefore for an identical subarea of a tissue under examination, the two attenuation values have to be caused by the same type of material or tissue. The coordinates ($\rho$, Z) of the curve intersection 17 therefore indicate the material density and the atomic number of the tissue subarea to be assigned to the image element.

Finally in step S327 the atomic number value Z thus obtained is written into the atomic number distribution as a corresponding image element value and in step S328 the determined material density value $\rho$ is written into the density distribution in a similar manner. Steps S322 to S328 are repeated for all remaining image points, until a final image can be output optionally in step S329. Step S324 can thereby be omitted, as the spectral distributions $S_i$ (E) and $w_i$ (E) are identical for all image elements of an image.

Figure 7:
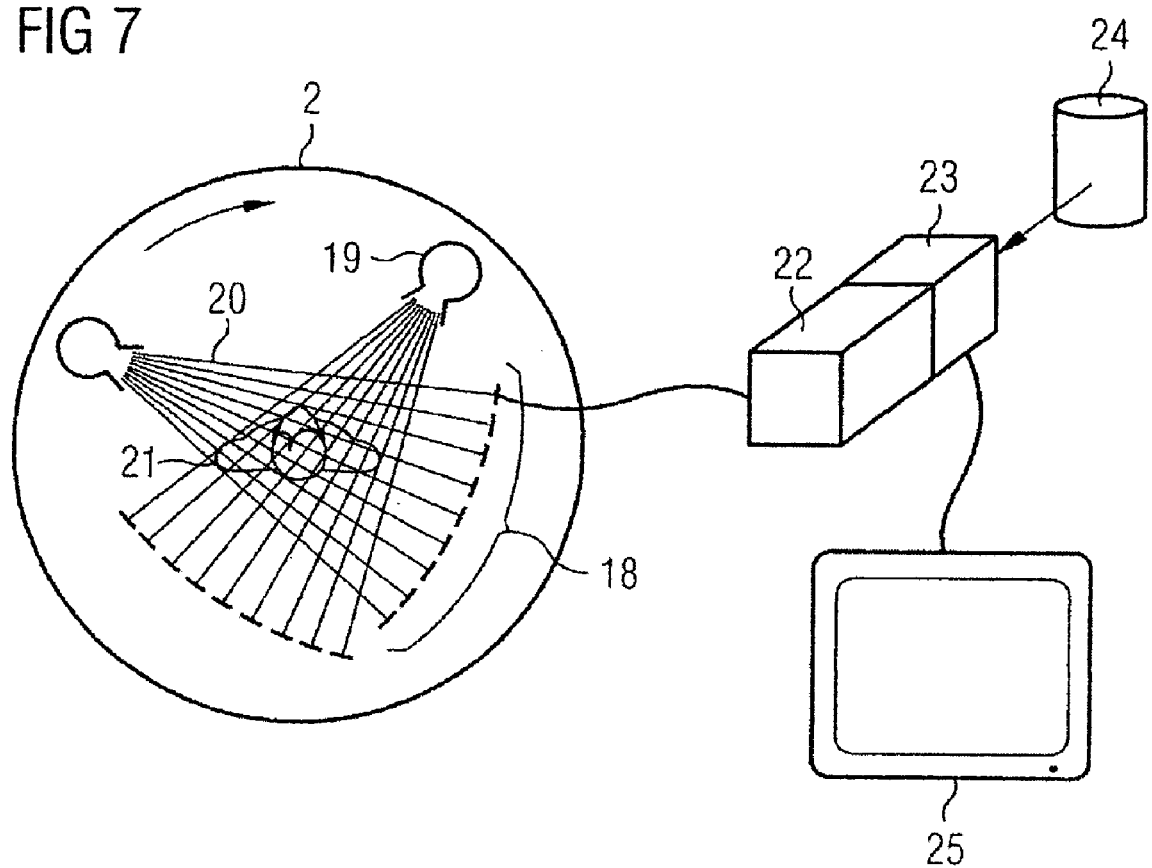
FIG. 7 shows a schematic illustration of the basic structure of the present device according to an exemplary embodiment.

FIG. 7 finally shows a highly schematic illustration of the basic structure of the present device with reference to an exemplary embodiment. This Figure shows an X-ray CT device 2 with a rotating detector system 18. The fan-shaped X-ray beams 20 emitted by the X-ray tube 19 transmit light through the object under examination 21 from a specific angle and finally arrive at a row of discrete detectors. A recording cycle comprises a plurality of such fluoroscopy operations at different angles in respect of the object under examination. The electrical signals supplied by the X-ray detectors 18 are converted by an evaluation unit 22 to X-ray attenuation data.

In the present example this evaluation unit 22 has a module 23 for fluid determination, which uses the X-ray attenuation data from one or a plurality of X-ray recordings of an object area including the fluid mass in the object 21, acquired with at least two different X-ray spectra, to determine values for effective atomic number and density for the fluid mass and averages each of these to obtain a mean value for the effective atomic number and density of the fluid mass. The mean values are then compared by the module 23 with comparison data, which is retrieved from a storage unit 24. The fluctuation range established in the comparison data is hereby defined, into which the two mean values fall, and a reference to the fluid type is output on a monitor 25, which is assigned to the fluctuation range determined in this manner.

Exemplary embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. Method for determining the type of fluid in a fluid mass in an object, comprising:
    supplying X-ray attenuation data from one or a plurality of X-ray recordings of an object area, including the fluid mass in the object;
    acquiring the data with at least two different X-ray spectra or detector weightings;
    using the X-ray attenuation data to determine values for effective atomic number and density for the fluid mass;
    averaging the values to obtain a mean value for effective atomic number and density for the fluid mass;
    supplying comparison data, indicative of fluctuation ranges for combinations of effective atomic number and density for different types of fluid;
    comparing the mean values for effective atomic number and density with the comparison data, to determine the fluctuation range, within which the two mean values fall; and
    determining the type of fluid that is assigned to the established fluctuation range.

2. Method according to claim 1, wherein the comparison data is obtained by preliminary measurement of a plurality of specimens for each of the different fluid types.

3. Method according to claim 2, wherein the supplying of the X-ray attenuation data includes taking the one or a plurality of X-ray recordings.

4. Method according to claim 1, wherein, to determine the values for effective atomic number and density for the fluid mass from the X-ray attenuation data, first data is defined, which represents a spatial distribution of effective atomic number and density in the object area, the fluid mass is identified in this data and segmented and then averaged over the segmented data, to obtain the mean values for effective atomic number and density for the fluid mass.

5. Method according to claim 4, wherein the supplying of the X-ray attenuation data includes taking the one or a plurality of X-ray recordings.

6. Method according to claim 1, wherein the supplying of the X-ray attenuation data includes taking the one or a plurality of X-ray recordings.

7. Device for determining the type of fluid in a fluid mass in an object, comprising:
    an X-ray source for emitting X-ray radiation;
    a plurality of X-ray detectors, facing the X-ray source, for acquiring X-ray attenuation data for the object arranged between the X-ray source and the X-ray detectors; and
    an evaluation unit for converting electrical signals from the X-ray detectors to X-ray attenuation data, wherein the evaluation unit includes a module for fluid determination, which uses X-ray attenuation data, from one or a plurality of X-ray recordings of an object area including the fluid mass in the object and acquired with at least two different X-ray spectra or detector weightings, to determine values for effective atomic number and density for the fluid mass, which averages these to obtain a mean value for effective atomic number and density for the fluid mass, which compares the mean values with comparison data in a storage unit, which indicates the fluctuation ranges of combinations of effective atomic number and density for different types of fluid to determine the fluctuation range, into which the two mean values fall, and which outputs a reference to the type of fluid, assigned to the defined fluctuation range.

8. Device according to claim 7, wherein the X-ray source includes at least two operating states, whereby in a first operating state, the X-ray source emits one of the two X-ray spectra and in a second operating state, the X-ray source emits the other of the two X-ray spectra.

9. Device according to claim 8, wherein the X-ray detectors are configured such that they convert spectral subareas of the X-ray radiation received from the X-ray source to mutually independent electrical signals.

10. Device according to claim 7, wherein the X-ray detectors are configured such that they convert spectral subareas of the X-ray radiation received from the X-ray source to mutually independent electrical signals.

11. Device for determining the type of fluid in a fluid mass in an object, comprising:
    means for supplying X-ray attenuation data from one or a plurality of X-ray recordings of an object area, including the fluid mass in the object;
    means for acquiring the data with at least two different X-ray spectra or detector weightings; and
    means for using the X-ray attenuation data to determine values for effective atomic number and density for the fluid mass, for averaging the values to obtain a mean value for effective atomic number and density for the fluid mass, for supplying comparison data, indicative of fluctuation ranges for combinations of effective atomic number and density for different types of fluid, for comparing the mean values for effective atomic number and density with the comparison data, to determine the fluctuation range, within which the two mean values fall, and for determining the type of fluid that is assigned to the established fluctuation range.

12. Device according to claim 11, wherein the comparison data is obtained by preliminary measurement of a plurality of specimens for each of the different fluid types.

13. Device according to claim 11, wherein, to determine the values for effective atomic number and density for the fluid mass from the X-ray attenuation data, first data is defined, which represents a spatial distribution of effective atomic number and density in the object area, the fluid mass is identified in this data and segmented and then averaged over the segmented data, to obtain the mean values for effective atomic number and density for the fluid mass.

14. Device according to claim 11, wherein the supplying of the X-ray attenuation data includes taking the one or a plurality of X-ray recordings.

* * * * *